(12) United States Patent
Williams et al.

(10) Patent No.: US 8,632,594 B2
(45) Date of Patent: Jan. 21, 2014

(54) INTERVERTEBRAL DEVICE AND METHOD OF USE

(75) Inventors: Lytton A. Williams, Los Angeles, CA (US); Sui-Kay Wong, North Point (HK)

(73) Assignees: Infinity Orthopaedics Company, Ltd, Fanling, N.T. (HK); IMDS Corporation, Providence, UT (US)

( * ) Notice: Subject to any disclaimer, the term of this patent is extended or adjusted under 35 U.S.C. 154(b) by 1473 days.

(21) Appl. No.: 11/461,509

(22) Filed: Aug. 1, 2006

(65) Prior Publication Data

US 2007/0010887 A1 Jan. 11, 2007

Related U.S. Application Data

(62) Division of application No. 10/402,123, filed on Mar. 28, 2003, now Pat. No. 7,717,959.

(60) Provisional application No. 60/368,783, filed on Mar. 30, 2002, provisional application No. 60/381,529, filed on May 16, 2002.

(51) Int. Cl.
*A61F 2/44* (2006.01)

(52) U.S. Cl.
USPC .................................... 623/17.15; 623/17.14

(58) Field of Classification Search
USPC ........................................... 623/17.11–17.16
See application file for complete search history.

(56) References Cited

U.S. PATENT DOCUMENTS

| | | | |
|---|---|---|---|
| 3,875,595 A | 4/1975 | Froning | |
| 4,309,777 A | 1/1982 | Patil | |
| 4,349,921 A | 9/1982 | Kuntz | |
| 4,401,112 A | 8/1983 | Rezaian | |
| 4,501,269 A | 2/1985 | Bagby | |
| 4,553,273 A | 11/1985 | Wu | |
| 4,554,914 A | 11/1985 | Kapp | |
| 4,599,086 A | 7/1986 | Doty | |
| 4,627,853 A | 12/1986 | Campbell | |
| 4,636,217 A | 1/1987 | Ogilvie | |
| 4,678,470 A | 7/1987 | Nashef | |
| 4,714,469 A | 12/1987 | Kenna | |
| 4,743,256 A | 5/1988 | Brantigan | |
| 4,743,259 A | 5/1988 | Bolander | |
| 4,759,769 A | 7/1988 | Hedman | |
| 4,834,757 A | 5/1989 | Brantigan | |
| 4,863,476 A | 9/1989 | Shepperd | |

(Continued)

FOREIGN PATENT DOCUMENTS

| | | |
|---|---|---|
| EP | 188954 A1 | 7/1986 |
| EP | 538183 A1 | 4/1993 |

(Continued)

OTHER PUBLICATIONS

ProDisc, Spine Solutions; Product Brochure p. 1-10.

*Primary Examiner* — Thomas J Sweet
*Assistant Examiner* — Cheryl Miller
(74) *Attorney, Agent, or Firm* — G. Jo Hays; James Larson; James M. Pinkstor

(57) ABSTRACT

An intervertebral disc replacement device is disclosed and includes a first implantable member having a first anchor plate and a concave body detachably coupled to the first anchor plate, and a second implantable member having a second anchor plate and a convex body detachably coupled to the second anchor plate, the convex body configured to engage the concave body in movable relation thereto.

7 Claims, 13 Drawing Sheets

(56) References Cited

U.S. PATENT DOCUMENTS

| | | |
|---|---|---|
| 4,878,915 A | 11/1989 | Brantigan |
| 4,892,545 A | 1/1990 | Day |
| 4,932,975 A | 6/1990 | Main |
| 4,961,740 A | 10/1990 | Ray |
| 4,997,432 A | 3/1991 | Keller |
| 5,015,247 A | 5/1991 | Michelson |
| 5,026,373 A | 6/1991 | Ray |
| 5,055,104 A | 10/1991 | Ray |
| 5,059,193 A | 10/1991 | Kuslich |
| 5,062,850 A | 11/1991 | MacMillan |
| 5,071,437 A | 12/1991 | Steffee |
| 5,123,926 A | 6/1992 | Pisharodi |
| 5,147,402 A | 9/1992 | Bohler |
| 5,192,327 A | 3/1993 | Brantigan |
| 5,236,460 A | 8/1993 | Barber |
| 5,258,031 A | 11/1993 | Salib |
| 5,263,953 A | 11/1993 | Bagby |
| 5,290,312 A | 3/1994 | Kojimoto |
| 5,306,310 A | 4/1994 | Siebels |
| 5,314,477 A | 5/1994 | Marnay |
| 5,336,223 A | 8/1994 | Rogers |
| 5,370,697 A | 12/1994 | Baumgartner |
| 5,397,364 A | 3/1995 | Kozak |
| 5,401,269 A | 3/1995 | Buttner-Janz |
| 5,417,975 A | 5/1995 | Lussi |
| 5,425,769 A | 6/1995 | Snyders, Jr. |
| 5,425,773 A | 6/1995 | Boyd |
| 5,439,684 A | 8/1995 | Prewett |
| 5,455,231 A | 10/1995 | Constantz |
| 5,458,641 A | 10/1995 | Ramirez Jimenez |
| 5,464,439 A | 11/1995 | Gendler |
| 5,480,442 A | 1/1996 | Bertagnoli |
| 5,507,813 A | 4/1996 | Dowd |
| 5,507,816 A | 4/1996 | Bullivant |
| 5,510,396 A | 4/1996 | Prewett |
| 5,522,899 A | 6/1996 | Michelson |
| 5,534,030 A | 7/1996 | Navarro |
| 5,549,679 A | 8/1996 | Kuslich |
| 5,554,191 A | 9/1996 | Lahille |
| 5,585,116 A | 12/1996 | Boniface |
| 5,609,635 A | 3/1997 | Michelson |
| 5,645,591 A | 7/1997 | Kuberasampath |
| 5,653,763 A | 8/1997 | Errico |
| 5,658,335 A | 8/1997 | Allen |
| 5,665,122 A | 9/1997 | Kambin |
| 5,676,701 A | 10/1997 | Yuan |
| 5,683,465 A | 11/1997 | Shinn |
| 5,693,100 A | 12/1997 | Pisharodi |
| 5,702,391 A | 12/1997 | Lin |
| 5,702,450 A | 12/1997 | Bisserie |
| 5,702,453 A | 12/1997 | Rabbe |
| 5,702,455 A | 12/1997 | Saggar |
| 5,713,904 A | 2/1998 | Errico |
| 5,749,916 A | 5/1998 | Richelsoph |
| 5,776,197 A | 7/1998 | Rabbe |
| 5,776,199 A | 7/1998 | Michelson |
| 5,782,832 A | 7/1998 | Larsen |
| 5,800,550 A | 9/1998 | Sertich |
| 5,888,227 A | 3/1999 | Cottle |
| 5,899,941 A | 5/1999 | Nishijima |
| 5,916,267 A | 6/1999 | Tienboon |
| 5,980,522 A | 11/1999 | Koros et al. |
| 5,989,290 A | 11/1999 | Biedermann |
| 6,015,436 A | 1/2000 | Schonhoffer |
| 6,045,579 A | 4/2000 | Hochshuler |
| 6,080,193 A | 6/2000 | Hochshuler |
| 6,102,950 A | 8/2000 | Vaccaro |
| 6,106,557 A | 8/2000 | Robioneck |
| 6,113,638 A | 9/2000 | Williams |
| 6,176,881 B1 | 1/2001 | Schar |
| 6,176,882 B1 | 1/2001 | Biedermann et al. |
| 6,217,579 B1 | 4/2001 | Koros |
| 6,344,057 B1 | 2/2002 | Rabbe |
| 6,368,350 B1 * | 4/2002 | Erickson et al. ............ 623/17.14 |
| 6,375,681 B1 | 4/2002 | Truscott |
| 6,375,683 B1 | 4/2002 | Crozet |
| 6,402,785 B1 | 6/2002 | Zdeblick |
| 6,419,704 B1 | 7/2002 | Ferree |
| 6,524,641 B1 | 2/2003 | de Witzmann |
| 6,572,653 B1 * | 6/2003 | Simonson ................. 623/17.13 |
| 6,576,016 B1 | 6/2003 | Hochshuler et al. |
| 6,595,998 B2 * | 7/2003 | Johnson et al. ................. 606/90 |
| 6,641,614 B1 | 11/2003 | Wagner et al. |
| 6,706,070 B1 | 3/2004 | Wagner et al. |
| 6,726,720 B2 | 4/2004 | Ross et al. |
| 6,899,735 B2 * | 5/2005 | Coates et al. .............. 623/17.16 |
| 6,936,071 B1 * | 8/2005 | Marnay et al. ............. 623/17.15 |
| 7,708,776 B1 * | 5/2010 | Blain et al. ................. 623/17.14 |
| 2002/0161441 A1 | 10/2002 | Lang |
| 2003/0204261 A1 * | 10/2003 | Eisermann et al. ........ 623/17.14 |
| 2003/0208272 A1 | 11/2003 | Crozet |
| 2004/0260396 A1 | 12/2004 | Ferree et al. |
| 2005/0060034 A1 | 3/2005 | Berry et al. |
| 2006/0122703 A1 * | 6/2006 | Aebi et al. ................. 623/17.15 |

FOREIGN PATENT DOCUMENTS

| | | |
|---|---|---|
| EP | 610837 A1 | 8/1994 |
| EP | 425542 B1 | 3/1995 |
| EP | 1161205 A1 | 8/2000 |
| WO | WO9214423 A1 | 9/1992 |
| WO | WO9310725 A2 | 6/1993 |
| WO | WO9700054 A1 | 1/1997 |
| WO | WO0049977 C2 | 8/2000 |
| WO | WO0217825 A2 | 3/2002 |

* cited by examiner

INTERVERTEBRAL DEVICE AND METHOD OF USE

CROSS-REFERENCE TO RELATED APPLICATIONS

This application is a divisional of:

U.S. application Ser. No. 10/402,123, filed Mar. 28, 2003, now U.S. Pat. No. 7,717,959 and entitled INTERVERTEBRAL DEVICE AND METHOD OF USE, and claims the benefit of:

U.S. Provisional Application Ser. No. 60/368,783, filed Mar. 30, 2002 and entitled METHOD AND APPARATUS FOR INTERVERTEBRAL DISC REPLACEMENT DEVICE, and U.S. Provisional Application Ser. No. 60/381,529, filed May 16, 2002 and entitled ANTERIOR LATERAL APPROACH TO DISC REPLACEMENT.

The disclosures listed above are incorporated herein by reference.

BACKGROUND OF THE INVENTION

The human spine is a flexible structure comprised of thirty-three vertebrae separated by intervertebral discs. The intervertebral discs act as shock absorbers cushioning adjacent vertebrae and permitting bending between the vertebrae. Generally, an intervertebral disc is comprised of a nucleus pulposus, an annulus fibrosis, and end plates. The nucleus pulposus comprises an inner gel-like core which occupies 25-40% of the disc's total cross-sectional area. The annulus fibrosis is a collagen fiber composite structure that surrounds the nucleus pulposus and resists hoop, torsional and bending stresses applied to the disc. The cartilaginous end plates separate the disc from the vertebrae on either side of the disc.

Currently, back pain remains a major public health problem, especially among aged people. Persistent and severe back pain may debilitate and disable the sufferer. A common cause of such pain is frequently the result of intervertebral disc abnormalities. For example, damage to one or more of the vertebrae and/or one or more discs may result from trauma, exertion, injury, illness, or abuse. More specifically, disorders of the vertebrae and discs may include, but are not limited, to: (1) disruption of the disc annulus such as annular fissures; (2) chronic inflammation of the disc; (3) localized disc herniations with contained or escaped extrusions; and (4) instability of the vertebrae surrounding the disc.

Various approaches have been developed to treat back pain. For example, minor back pain may be treated with medication and other non-invasive therapies. However, severe back pain often necessitates the removal of at least a portion of the damaged and/or malfunctioning back component. Should the disc become ruptured, the ruptured disc may be surgically removed and the two adjacent vertebrae proximate to the removed disc may be permitted to fuse together. Alternatively, the end plates of two adjacent vertebras may be fused posterior-laterally by screws or other fusing devices. While these fusion procedures have proven successful in treating some intervertebral dysfunctions, several shortcomings have been discovered. For example, pseudoarthrosis may result from such posterior fusion procedures.

In light of the foregoing, there is an ongoing need for an implantable intervertebral device capable of simulating the natural movement of the vertebrae.

SUMMARY OF THE INVENTION

The present application relates to a variety intervertebral devices which can implanted within the spine of a patient by a variety of methods to treat a variety of indications.

An embodiment of an intervertebral disc replacement device is disclosed and includes a first implantable member having a first anchor plate and a concave body detachably coupled to the first anchor plate, and a second implantable member having a second anchor plate and a convex body detachably coupled to the second anchor plate, the convex body configured to engage the concave body in movable relation thereto.

In another embodiment, an intervertebral device is disclosed and includes a first implantable member having a first anchor plate disposing a plurality of anchoring elements positioned on a periphery of the first anchor plate, and a concave body detachably coupled to the first anchor plate, and a second implantable member having a second anchor plate disposing a plurality of anchoring elements positioned on a periphery of the second anchor plate, and a convex body detachably coupled to the second anchor plate, the convex body configured to engage the concave body in movable relation thereto.

In yet another embodiment, a partial disc replacement device is described and includes a first partial disc device having a first anchor plate disposing a plurality of anchoring elements positioned on a periphery of the first anchor plate, and a hemi-concave body detachably coupled to the first anchor plate, and a second partial disc device having a second anchor plate disposing a plurality of anchoring elements positioned on a periphery of the second anchor plate, and a hemi-convex body detachably coupled to the second anchor plate, the hemi-convex body configured to engage the hemi-concave body in movable relation thereto.

In addition, a method of implanting an intervertebral disc prosthesis within the spine of a patient is described and includes providing a disc space between two adjacent vertebrae, positioning at least one intervertebral disc prosthesis within the disc space, and engaging a cartilaginous end plate of a vertebra with at least one anchoring element positioned on the intervertebral disc prosthesis.

In another embodiment, a method of implanting an intervertebral disc prosthesis within the spine of a patient is disclosed and includes providing a disc space between two adjacent vertebrae, positioning a first implantable member having a concave recess formed therein within the disc space, engaging a cartilaginous end plate of a vertebra with at least one anchoring element positioned on the first implantable member, positioning a second implantable member having a convex body formed thereon within the disc space, engaging a cartilaginous end plate of a vertebra with at least one anchoring element positioned on the second implantable member, and engaging the concave body of the first implantable member within the convex body of the second implantable member.

In yet another embodiment, a method of repairing an intervertebral disc prosthesis implanted within the body of a patient is disclosed and includes providing a disc space between two adjacent vertebrae, a first vertebra having a first implantable member implanted therein, the first implantable member having a concave body coupled thereto, and a second vertebra having a second implantable member implanted therein, the second implantable member having a convex C body coupled thereto, removing a coupling member coupling the concave body to the first implantable member, removing the concave body from the first implantable member while leaving a first anchor plate implanted within the first vertebra, positioning a replacement concave body on the first anchor plate, coupling the replacement concave body to the first anchor plate with a coupling member, and engaging the replacement concave body of the first implantable member with the convex body of the second implantable member.

In addition, an anterior lateral method of accessing the vertebrae of a patient is described herein and includes positioning a patient in a lateral decubitus position, determining a position of a disc to be accessed within the spine, forming an incision within the skin of a patient from a mid-axilliary line medially and laterally over a disc space to be repaired, incising a subcutaneous tissue and underlying fascia, bluntly dissecting an external oblique muscle, bluntly dissecting a transversus, bluntly dissecting an internal oblique muscle, bluntly dissecting a peritoneum posteriorly to the vertebrae, bluntly dissecting a psoas anteriorly and posteriorly without injuring a lumbrosacral plexus or nerve root, retracting the peritoneum medially and cephalad to the vertebra, ligating segmented vessels, and retracting medially and laterally the ligated segmented vessel to permit access to the vertebra.

Other objects, features, and advantages of the present invention will become apparent from a consideration of the following detailed description.

BRIEF DESCRIPTION OF THE DRAWINGS

FIG. 28 shows a perspective view of a vertebral disc positioned between two adjacent vertebras;

FIG. 29 shows a perspective view of a vertebral disc positioned between two adjacent vertebras separated a distance D6;

FIG. 30 shows a perspective view of two adjacent vertebras separated a distance D6;

FIG. 31 shows a perspective view of an embodiment of a second implantable member of an intervertebral disc replacement device positioned between two adjacent vertebras;

FIG. 32 shows a perspective view of an embodiment of a second implantable member of an intervertebral disc replacement device coupled to a vertebra;

FIG. 33 shows a perspective view of an embodiment of a first implantable member of an intervertebral disc replacement device positioned between two adjacent vertebras;

FIG. 34 shows a perspective view of an embodiment of a first implantable member of an intervertebral disc replacement device coupled to a vertebra;

FIG. 35 shows a perspective view of an embodiment of a first implantable member coupled to a vertebra engaging a second implantable member coupled to an adjacent vertebra;

FIG. 36 shows another perspective view of an embodiment of a first implantable member coupled to a vertebra engaging a second implantable member coupled to an adjacent vertebra;

FIG. 37 shows a perspective view of a second implantable member coupled to a vertebra prior to convex body replacement;

FIG. 38 shows a perspective view of a second implantable member coupled to a vertebra during convex body replacement wherein the convex body has been removed;

FIG. 39 shows a perspective view of a second implantable member coupled to a vertebra during convex body replacement wherein the replacement convex body is positioned within the disc space;

FIG. 40 shows a perspective view of an embodiment of a first implantable member coupled to a vertebra engaging a second implantable member coupled to an adjacent vertebra;

FIG. 41 shows a perspective view of an embodiment of a first implantable member g coupled to a vertebra engaging a second implantable member coupled to an adjacent vertebra prior to a disc fusion procedure;

FIG. 42 shows a perspective view of an embodiment of a first anchor plate and second anchor plate each coupled to a vertebra prior to coupling a disc fusion device thereto; and FIG. 43 shows a perspective view of an embodiment of a first anchor plate and second anchor plate each coupled to a vertebra prior having a disc fusion device coupled thereto.

DETAILED DESCRIPTION

An intervertebral disc replacement device is disclosed herein which may be implanted into the spine of mammalian body. Unlike previous disc prosthesis which include attachment devices that engage the nucleous pulposus or annulus fibrosus of the vertebra disc, the disc prosthesis disclosed herein includes at least one anchor plate having one or more anchoring elements positioned thereon which are configured to engage and couple the disc replacement device to the cartilaginous vertebrae end plates of the spine, thereby enhancing the device stability once implanted. In addition, the intervertebral disc replacement device disclosed herein may include replaceable components thereby enabling a surgeon to customize the fit of each device to each patient's physiological constraints and changing physiological condition. In addition, the intervertebral disc replacement device may be manufactured in a variety of sizes, thereby permitting the device to be implanted at a variety of locations within the spine of the patient. For example, in one embodiment, the intervertebral device may sized to be implanted within a lumbar region of a patient's spine. In another embodiment, the intervertebral device may be sized to be implanted within a cervical region of the patient's spine.

Figure 1:
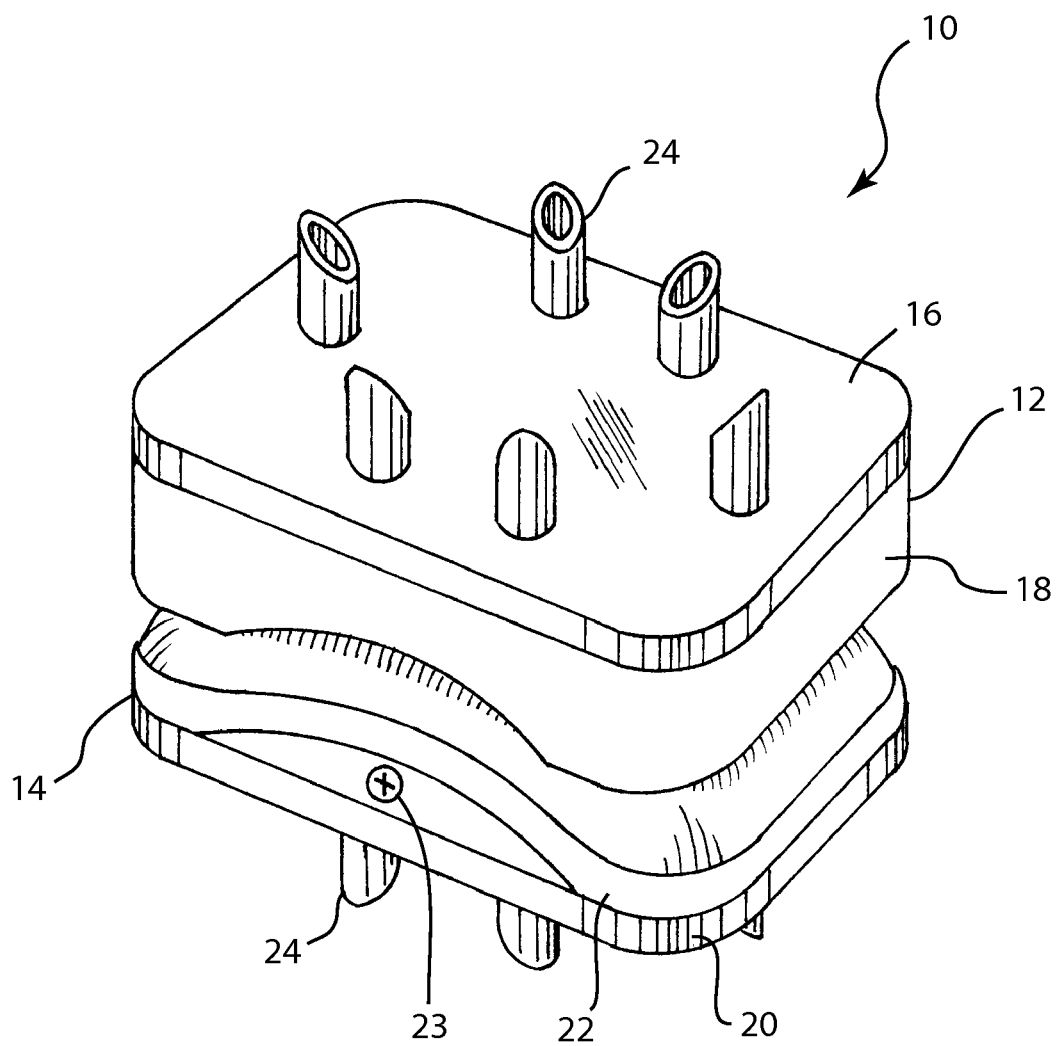
FIG. 1 shows a perspective view of an embodiment of an intervertebral disc replacement device.
Figure 2:
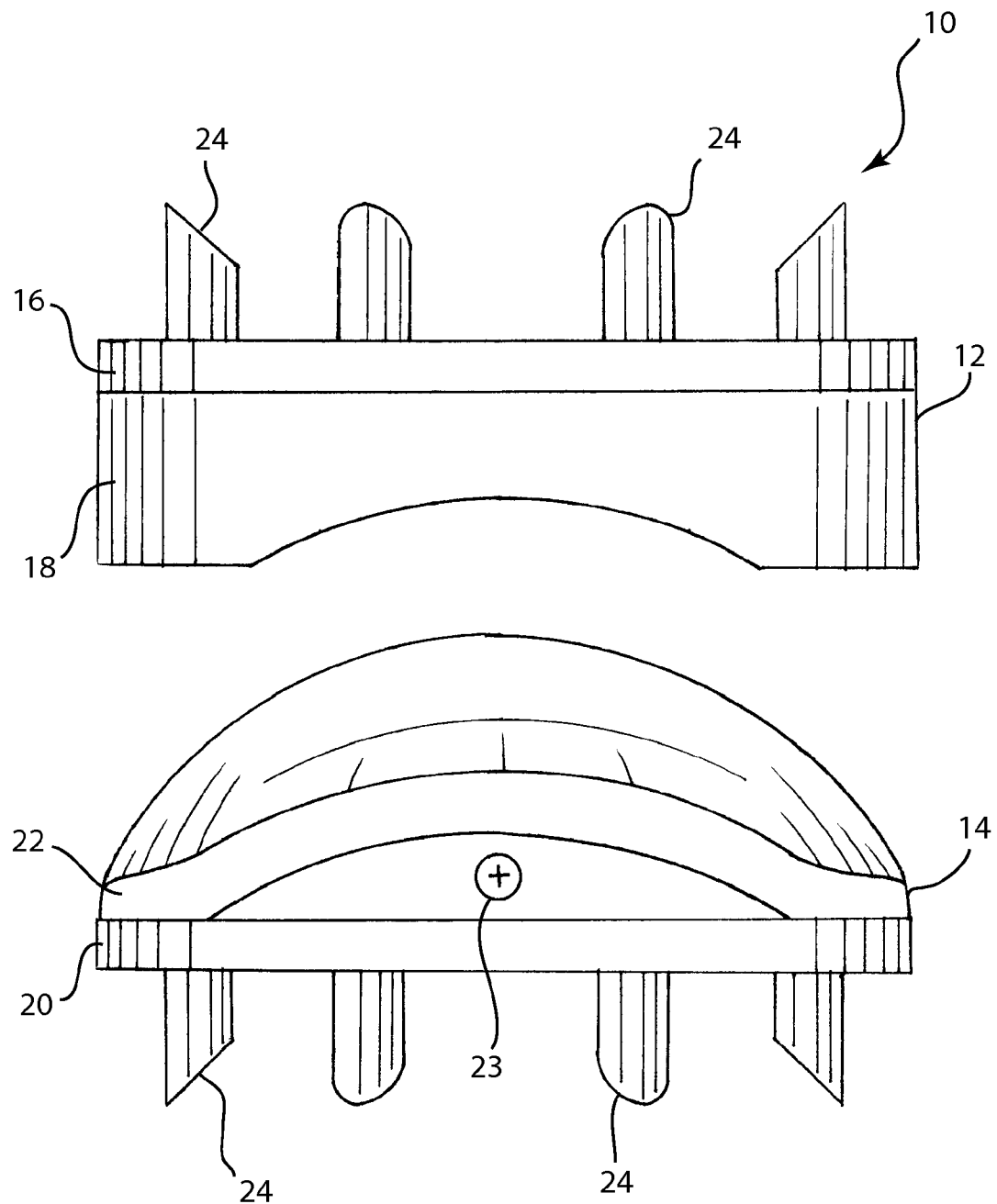
FIG. 2 shows a longitudinal side view of an embodiment of an intervertebral disc replacement device.

FIGS. 1 and 2 show various views of one embodiment of the intervertebral disc replacement device. As shown in FIG. 1, the intervertebral device 10 comprises a first implantable member 12 and second implantable member 14 sized to movable engage the first implantable member 12. The first implantable member 12 includes a first anchor plate 16 having a concave body 18 positioned thereon. Similarly, the second implantable member 14 comprises a second anchor plate 20 having a convex body 22 positioned thereon. Optionally, the convex body 22 may be detachably coupled to the second anchor plate 20 using, for example, a coupling member 23. Although not shown, the concave body 18 may be detachably coupled to first anchor plate 16 using a coupling member 23. Exemplary coupling members 23 may include, without limitation, screws including set screws, bolts, pins, lock members, buttons, toggles, friction retention devices, magnetic retention devices, and snap locks. Each of the first and second anchor plates 16, 20 may include one or more anchoring elements 24 extending therefrom. As shown in FIG. 1, the anchoring elements 24 may be positioned around the periphery of the first and second anchor plates 16, 20, thereby enabling the anchoring elements 24 to penetrate and be retained within the a mounting surface or structure. For example, the anchoring elements 24 may penetrate and be retained within the cartilaginous end plates of a vertebrae of a patient. The first implantable member 12, the second implantable member 14, or both may include a therapeutic agent or marking agent thereon. For example, the first implantable member 12, the second implantable member 14, or both may be plasma sprayed or include plasma sprayed or titanium bedded anchoring elements 24 thereon.

Figure 3:
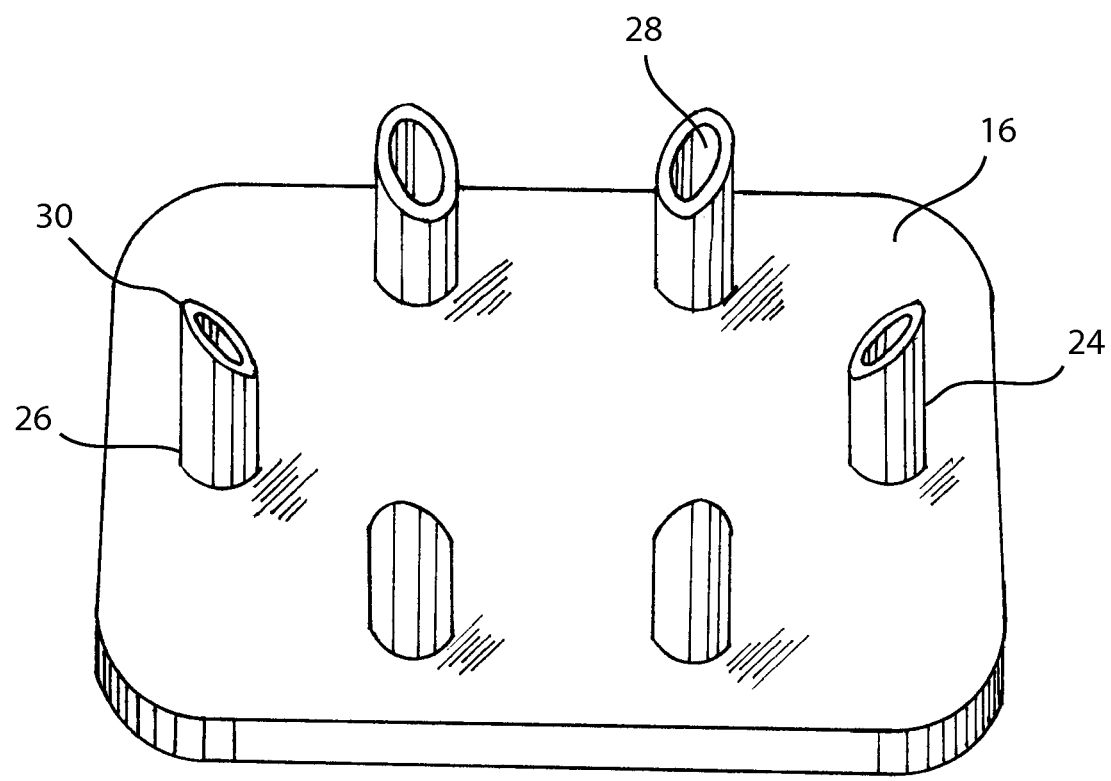
FIG. 3 shows an elevated view of an embodiment of an anchor plate of an intervertebral disc replacement device.

FIG. 3 shows a detailed view of the first anchor plate 16 having a plurality of anchoring elements 24 located on the periphery thereof. As shown in FIG. 3, the anchoring elements 24 comprise an anchor body 26 defining a anchor lumen 28. The anchor lumen 28 formed within the anchor body 26 may permit or promote the ingrowth of tissue or bone graft material into or through the anchor lumen 28, thereby securely coupling the first anchor plate 16 to the vertebrae. The anchoring element 24 may include a pointed or sharpened tip 30 which permits the anchor element 24 to penetrate tissue proximate thereto. For example, the pointed tip 30 of the anchoring element 24 facilitates the entry of the anchoring elements 24 into the end plates of a vertebra while limited or eliminating splintering of the vertebra during implantation. In another embodiment, the anchoring elements 24 may be constructed without pointed or sharpened tips, instead using rounded, blunted, or atraumatic tips.

As illustrated in FIG. 3, the anchor bodies 26 comprises a continuous wall defining the anchor lumen 28. Optionally, at least one anchor body 26, anchoring element 24, and/or anchor plates 16, 20 may include at least one port, slot, tab, button, fenestration, or other surface discontinuities thereon to aid in or promote tissue in-growth. For example, the interior surface defining the anchor lumen 28, the exterior surface of the anchor body 26, or both surfaces of the anchor body 26 may be porous or textured to promote tissue in-growth or smooth to facilitate penetration of the anchoring element 24 into the vertebrae. In another embodiment, the anchoring elements 24, the anchor plates 16, 20, or both, may include a coating, such as a Ti-plasma coating or flutes thereon thereby providing a textured surface.

The anchoring elements 24 positioned on the anchoring plates 16, 20 may be manufactured in a variety of lengths, diameters, or shapes. In one embodiment, the anchoring elements 24 are comprise a solid post or body. In an alternate embodiment, the anchor element 24 may comprise a hollow or tubular form. For example, the anchor lumen 28 formed in an anchoring element 24 may have a transverse dimension of about 0.5 mm to about 0.9 mm. In another embodiment, the distal portion 32 of the anchoring element 24 may be straight, curved, flared, converging, and/or may include a edge, lip, or undercut feature to enhance or improve tissue ingrowth. In yet another embodiment, the anchoring elements 24, the anchor plates 16, 20, or both, may dispose a therapeutic agent thereon. Exemplary therapeutic agents may include, for example, hydroxyapatite, bioactive proteins (e.g. bone morphogenic protein), or other therapeutic agents capable of promoting tissue in-growth. In an alternate embodiment, the anchor plates 16, 20 and/or the anchoring elements 24 disposed thereon may be plasma sprayed or may include titanium beds or points. Like the first anchor plate 16, the second anchor plate embodiment, the anchoring elements 24 may be constructed without pointed or sharpened tips, instead using rounded, blunted, or atraumatic tips.

As illustrated in FIG. 3, the anchor bodies 26 comprises a continuous wall defining the anchor lumen 28. Optionally, at least one anchor body 26, anchoring element 24, and/or anchor plates 16, 20 may include at least one port, slot, tab, button, fenestration, or other surface discontinuities thereon to aid in or promote tissue in-growth. For example, the interior surface defining the anchor lumen 28, the exterior surface of the anchor body 26, or both surfaces of the anchor body 26 may be porous or textured to promote tissue in-growth or smooth to facilitate penetration of the anchoring element 24 into the vertebrae. In another embodiment, the anchoring elements 24, the anchor plates 16, 20, or both, may include a coating, such as a Ti-plasma coating or flutes thereon thereby providing a textured surface.

The anchoring elements 24 positioned on the anchoring plates 16, 20 may be manufactured in a variety of lengths, diameters, or shapes. In one embodiment, the anchoring elements 24 are comprise a solid post or body. In an alternate embodiment, the anchor element 24 may comprise a hollow or tubular form. For example, the anchor lumen 28 formed in an anchoring element 24 may have a transverse dimension of about 0.5 mm to about 0.9 mm. In another embodiment, the distal portion 32 of the anchoring element 24 may be straight, curved, flared, converging, and/or may include a edge, lip, or undercut feature to enhance or improve tissue ingrowth. In yet another embodiment, the anchoring elements 24, the anchor plates 16, 20, or both, may dispose a therapeutic agent thereon. Exemplary therapeutic agents may include, for example, hydroxyapatite, bioactive proteins (e.g. bone morphogenic protein), or other therapeutic agents capable of promoting tissue in-growth. In an alternate embodiment, the anchor plates 16, 20 and/or the anchoring elements 24 disposed thereon may be plasma sprayed or may include titanium beds or points. Like the first anchor plate 16, the second anchor plate 20 may include anchoring elements 24 (see FIGS. 1-2) of similar design as previously described herein.

As shown in FIGS. 1-3, the anchoring elements 24 may extend perpendicularly from the anchor plates 16, 20. In an alternate embodiment, the anchoring elements 24 may extend from the first and second anchor plates 16, 20, respectively, at an angle and may be substantially straight, curved, tapered, flared, frusto-conical, or conical. The anchoring elements 24 may integrally formed or mechanically attached to the anchor plates 16, 20 using methods known in the art, such as, plasma welding. The first and second implantable members 12, 14, respectively, or any part thereof, may be manufactured from or otherwise incorporate a plurality of biologically-compatible materials, including, without limitation, titanium or titanium alloys, stainless steel, cobalt-chromium alloys, vanadium, ceramic or ceramic materials, such as aluminum oxide and zirconium oxide ceramic, Nickel Titanium alloys, shape memory alloys, plastics, carbon fiber reinforced polymers known commercially as "Peek" (polyetherether ketone) or "Ultrapeek" (polyether ketone, ether ketone, ketone), polycarbonate, polyprophylene, polyethylene, polysulfone plastics material filled with glass or carbon fibers Kevlar, composite material, various metallic alloys, elastomers, or other biologically-compatible, substantially chemically inert materials. In addition, the intervertebral device of the present invention may incorporate echogenic, radio-opaque, or radiolucent materials.

Figure 4:
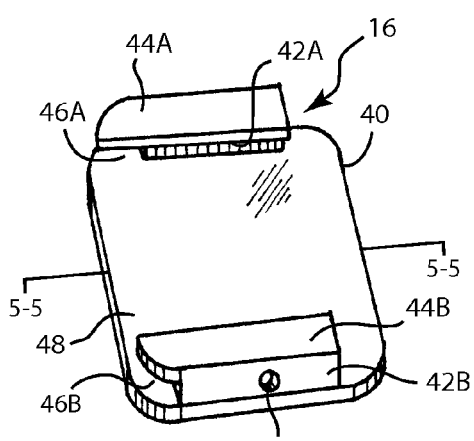
FIG. 4 shows a perspective view of an embodiment of a first anchor plate of an intervertebral disc replacement device with a concave body removed therefrom.
Figure 5:
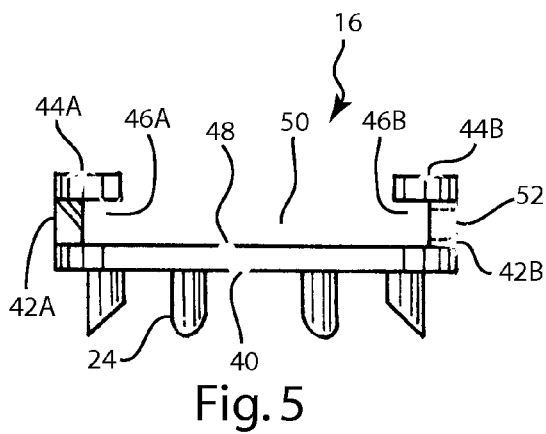
FIG. 5 shows a side view of an embodiment of a first anchor plate of an intervertebral disc replacement device with a concave body removed therefrom taken along the line 5-5 as shown in FIG. 4.
Figure 7:
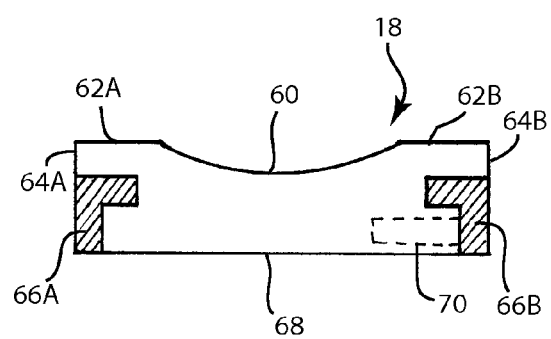
FIG. 7 shows a side view of an embodiment of a concave body of an intervertebral disc replacement device removed from a first anchor plate taken along the line 7-7 as shown in FIG. 6.
Figure 8:
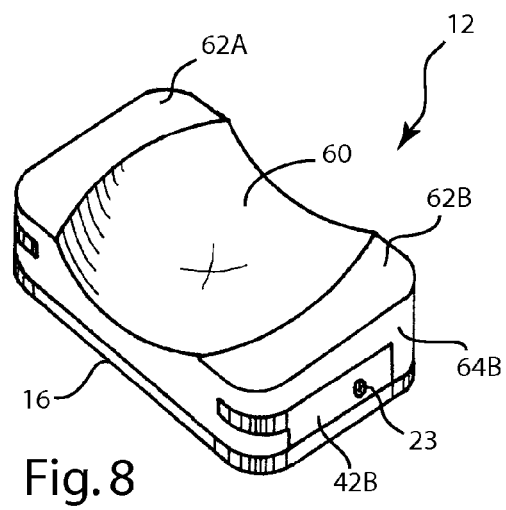
FIG. 8 shows a perspective view of an embodiment of a first implantable member of an intervertebral disc replacement device.

FIGS. 4-8 show the various components of the first implantable member 12. As shown in FIGS. 4 and 5, the first anchor plate 16 includes a base plate 40 configured to receive and support one or more anchoring elements 24 thereon. The base plate 40 is in communication with a first and second retaining wall 42A, 42B, respectively. A first retaining flange 44A is integral with, coupled to, or otherwise in communication with the first retaining wall 42A thereby defining a first retaining recess 46A. Similarly, a second retaining flange 44B is integral with, coupled to, or otherwise in communication with the second retaining wall 42B, thereby defining a second retaining recess 46B. An interior surface 48 of the base plate 40 further defines the first and second retaining recesses 46A, 46B, respectively. As a result, a concave body receiver 50 is formed by the interior surface 48 of the base plate 40, the first and second retaining walls 42A, 42B, and the first and second retaining flanges 44A, 44B. As shown in FIG. 4, at least one coupling member recess 52 may be formed on first retaining wall 42A, the second retaining wall 42B, or both retaining walls. Alternatively, at least one coupling member recess 52 may be formed on any of the aforementioned components of the first anchor plate 16.

Figure 6:
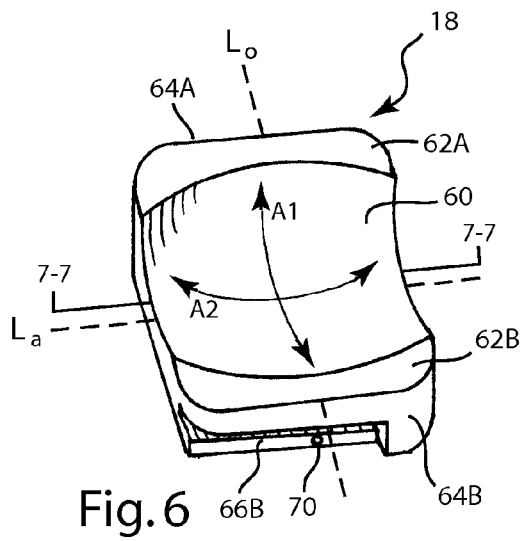
FIG. 6 shows a perspective view of an embodiment of a concave body of an intervertebral disc replacement device removed from a first anchor plate.
Figure 9:
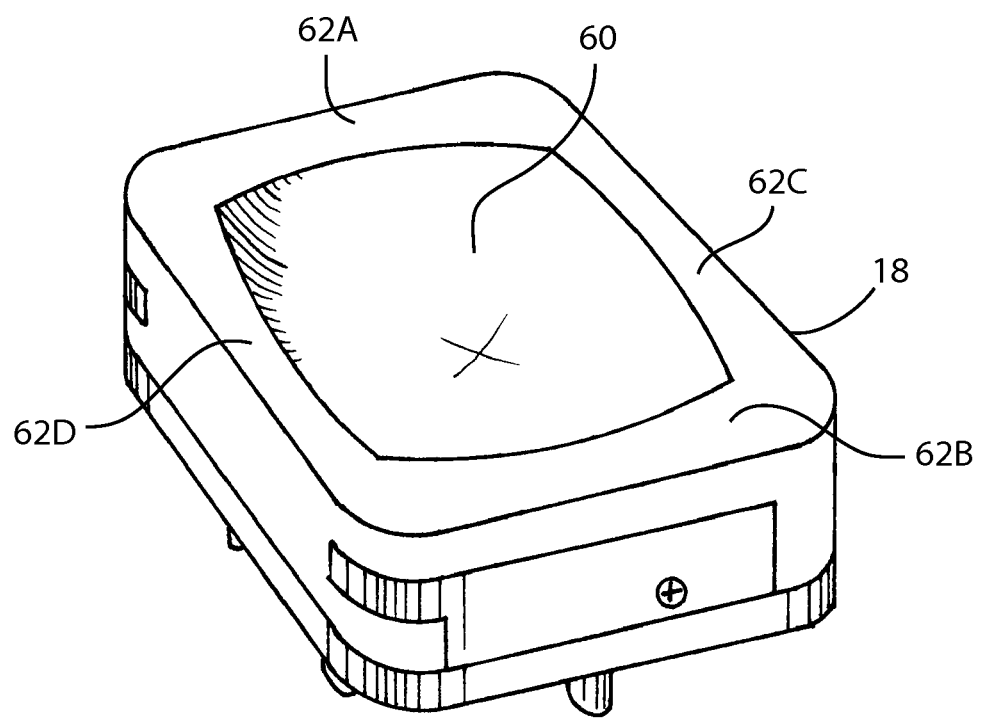
FIG. 9 shows a perspective view of another embodiment of a first implantable member of an intervertebral disc replacement device.

FIGS. 6-9 show the concave body 18 removed from the first anchor plate 16 (see FIGS. 4-5). The concave body 18 defines a concave recess 60 therein. As shown in FIG. 6, the concave recess 60 may define a longitudinal concave arc A1 co-aligned with the longitudinal axis $L_o$, a lateral concave arc A2 co-aligned with the lateral axis $L_a$, or both, thereby permitting the second implantable member 14 to freely move along concave arcs A1, A2, or both when engaging the first implantable member 12 (see FIG. 2). In the illustrated embodiment, the concave body 18 includes a first and second planar flange 62A, 62B, respectively, positioned proximate to the concave recess 60. As shown in FIG. 9, the concave body 18 may include four planar flanges 62A, 62B, 62C, 62D, respectively positioned proximate to the concave recess 60. The concave body 18 may be manufactured without a planar flange or, in the alternative, may be manufactured with any number of planar flanges positioned thereon. Referring again to FIGS. 6-9, the planar flanges 62A, 62B may define the concave recess 60. In addition, the planar flanges 62A, 62B may be configured to constrain or limit the longitudinal, lateral, rotational, arcuate, or transverse movement of the second implantable member 14 when engaging the first implantable member 12.

Referring again to FIGS. 6-8, the concave body 18 includes at least a first support wall 64A and a second support wall 64B. A first coupling track 66A is formed on the first support wall 64A. Similarly, a second coupling track 66B is formed on the second support wall 64B. A base member 68 is in communication with the first and second coupling tracks 66A, 66B. The first and second coupling tracks 66A, 66B are configured to be received within the concave body receiver 50 and engage the first and second retaining flanges 44A, 44B (see FIGS. 4 and 5), thereby detachably coupling the concave body 18 to the first anchor plate 16. A coupling member receiver 70, capable of receiving a coupling member 23 therein may be positioned on the any of the aforementioned components of the concave body 18.

In the illustrated embodiment, the concave body 18 includes coupling tracks 66A, 66B capable of engaging the first anchor plate 16 thereby detachably coupling the concave body 18 thereto. In an alternate embodiment, a variety of coupling devices known in the art may be used to detachably couple the concave body 18 to the first anchor plate 16 including, for example, friction fit devices, locking members, magnetic coupling devices, twist locks, or snap-fit devices.

Figure 10:
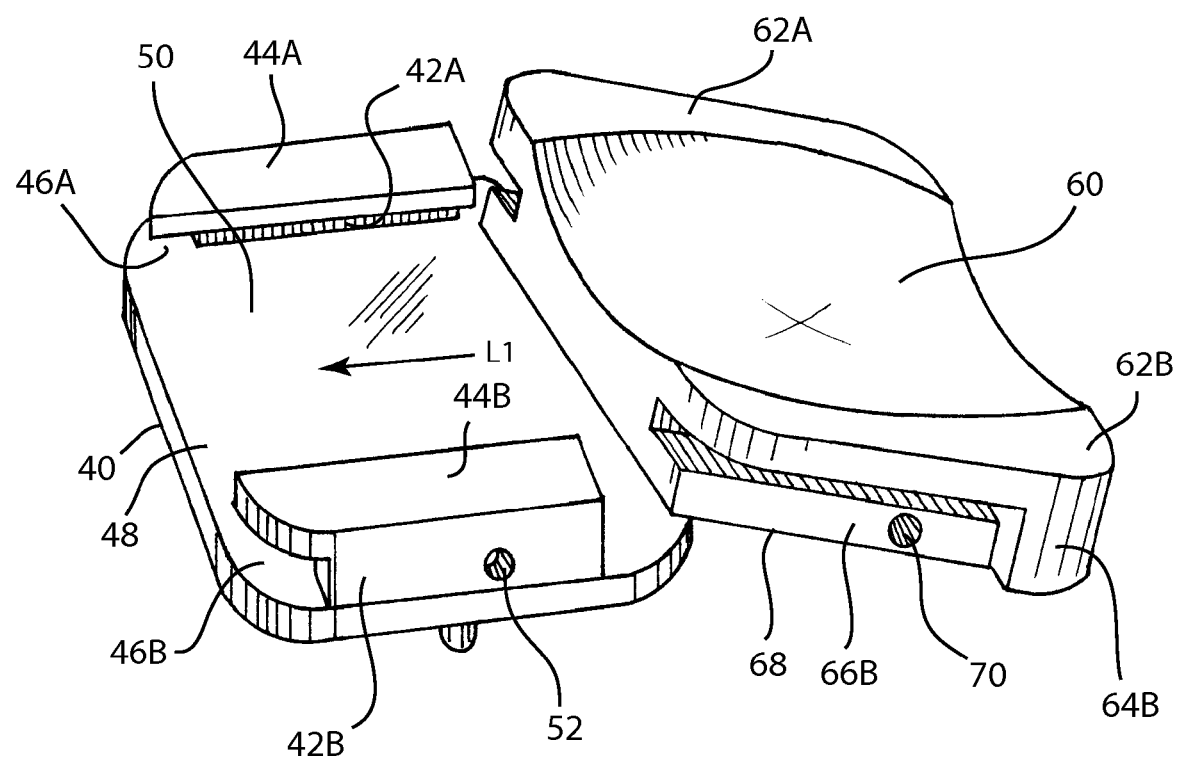
FIG. 10 shows a perspective view of an embodiment of a first implantable member of an intervertebral disc replacement device during assembly.
Figure 11:
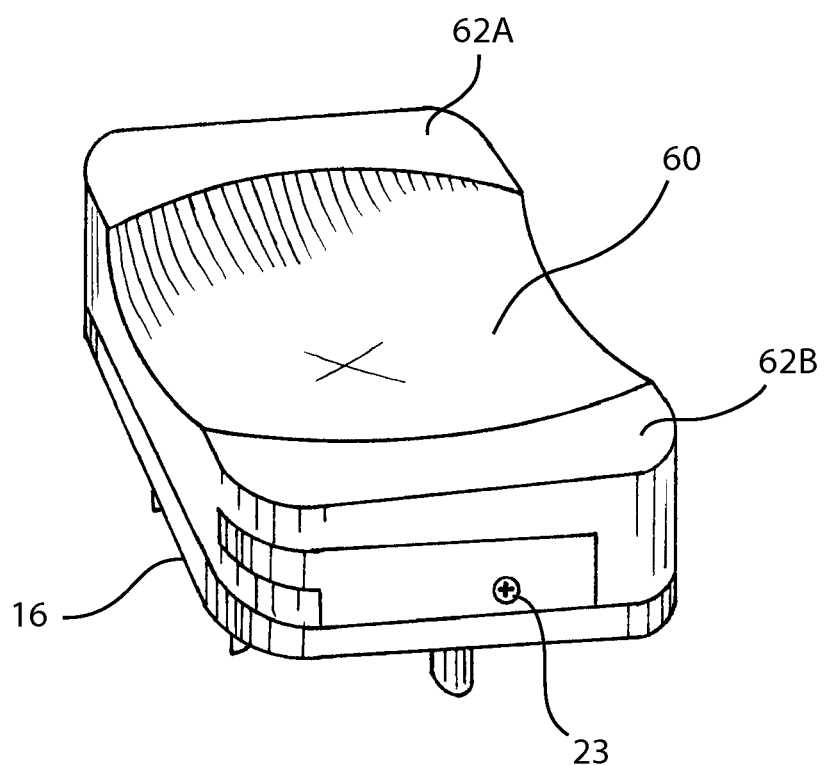
FIG. 11 shows a perspective view of an embodiment of an assembled first implantable member of an intervertebral disc replacement.

FIGS. 10 and 11 show the first implantable device 12 during various stages of assembly. As shown, the base member 68 of the concave body 18 is positioned proximate to the interior surface of the base plate 40 of the first anchor plate 16. Thereafter, the concave body 18 is advanced along line L1 as shown in FIG. 10, which results in the concave body 18 advancing into the concave body receiver 50 of the first anchor plate 16. The continued progress of the concave body 18 into the concave body receiver 50 results in first and second support walls 64A, 64B and first and second coupling tracks 66A, 66B engaging the first and second retaining walls 42A, 42B and first and second retaining flanges 44A, 44B, thereby detachably coupling the concave body 18 to the first anchor plate 16. A retractable or detachable coupling member 23 may be inserted into the coupling member recess 52 and coupling member receiver 70 (see FIGS. 4 and 6), thereby securing the concave body 18 to the first anchor plate 16. In the illustrated embodiment, the concave body 18 is configured to slidably engage and couple to the first anchor plate 16 along the lateral axis $L_a$. In an alternate embodiment, the concave body 18 may be configured to slidably engage and couple to the first anchor plate 16 along the longitudinal axis $L_o$.

Figure 12:
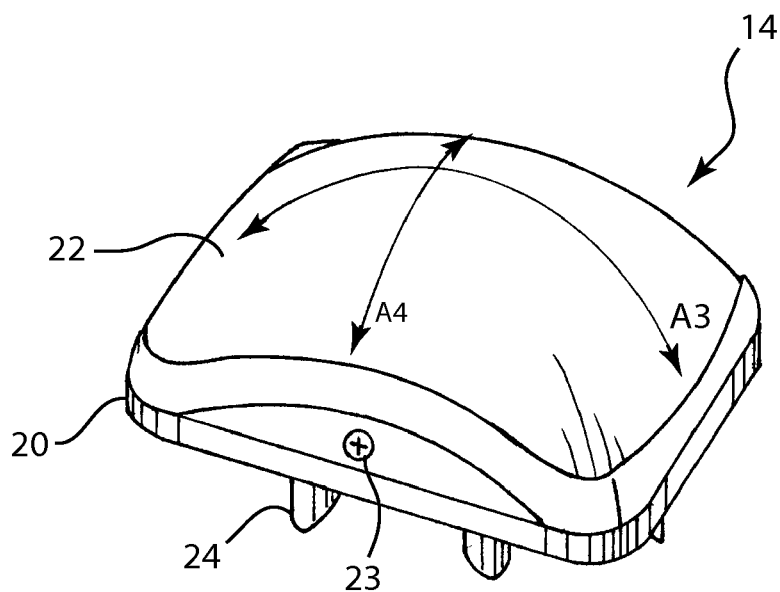
FIG. 12 shows a perspective view of an embodiment of a second implantable member of an intervertebral disc replacement device.

FIGS. 12-19 illustrate an embodiment of the second implantable member 14. As shown, the second implantable member 14 includes a second anchor plate 20 having a convex body 22 detachably coupled thereto. One or more anchoring elements 24 are positioned on or in communication with the second anchor plate 20. At least one coupling member 23 is used to secure the convex body 22 to the second anchor plate 20. As shown in FIG. 12, the convex body 22 may define a longitudinal convex arc A3, a lateral convex arc A4, or both, thereby permitting the convex body 22 of the second implantable member 14 to freely move within the concave body 18 when engaging the first implantable member 12 (see FIG. 8). The convex arcs A3 and A4 may be symmetrical, asymmetrical.

Figure 13:
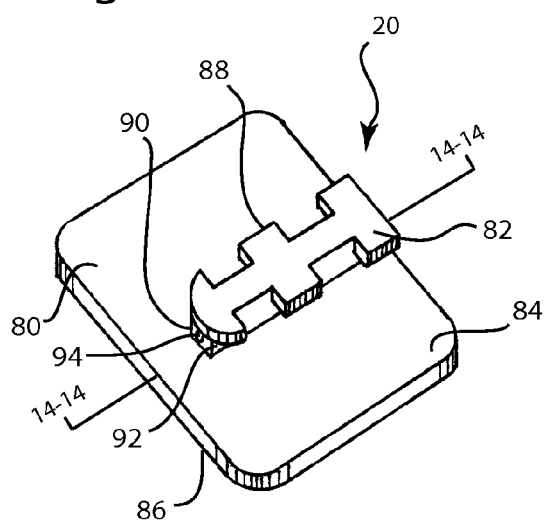
FIG. 13 shows a perspective view of an embodiment of a second anchor plate of an intervertebral disc replacement device with a convex body removed therefrom.
Figure 14:
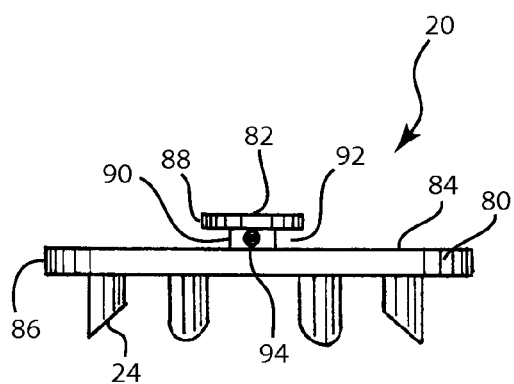
FIG. 14 shows a side view of an embodiment of a second anchor plate of an intervertebral disc replacement device with a convex body removed therefrom taken along the line 14-14 as shown in FIG. 13.

Referring to FIGS. 13 and 14, the second anchor plate 20 includes a base member 80 having a convex body receiver 82 positioned thereon. In one embodiment, the convex body receiver 82 may be integral with or attached to the interior surface 84 of the base member 80. The exterior surface 86 of the base member 80 may include one or more anchoring elements 24 located thereon. In the illustrated embodiment, the anchoring elements 24 are positioned on the periphery of the exterior surface 86 of the base member 80 thereby permitting the anchoring elements 24 to engage and be retained within the cartilaginous end plates of a vertebrae of a patient. In the illustrated embodiment, one convex body receiver 82 is positioned on the interior surface 84 of the base plate 80. In an alternate embodiment, any number of convex body receivers 82 may be positioned on the interior surface 84 of the base member 80. The convex body receiver 82 may comprise a coupling flange 88 positioned on or in communication with a coupling body 90, thereby forming a coupling recess 92 configured to engage and retain the convex body 22 therein. The coupling flange 88 illustrated in FIG. 13 is slotted. However, the coupling flange 88 is not limited to the illustrated slotted configuration, and may be configured to allow the arcuate body 100 to be inserted laterally, longitudinally, or may vertically engage the coupling recess 92 thereby slidably engaging and coupling the convex body receiver 82 to the second anchor plate 20. In another embodiment, the coupling flange 88 may include or otherwise comprise a continuous flange, slot, or other coupling shape. At least one fastener receiver 94 capable of receiving a coupling member 23 (see FIG. 12) may be positioned on any of the components of the second anchor plate 20.

Figure 15:
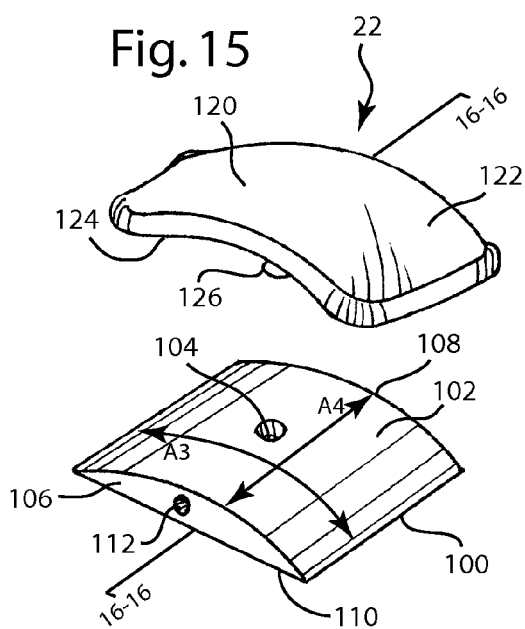
FIG. 15 shows a perspective view of an embodiment of a convex body of an intervertebral disc replacement device removed from a second anchor plate.
Figure 16:
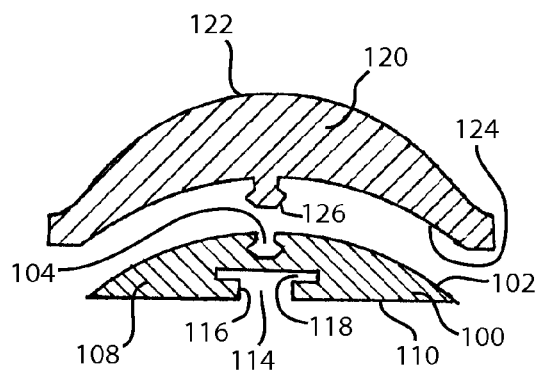
FIG. 16 shows a side view of an embodiment of a convex body of an intervertebral disc replacement device removed from a second anchor plate taken along the line 16-16 as shown in FIG. 15.
Figure 17:
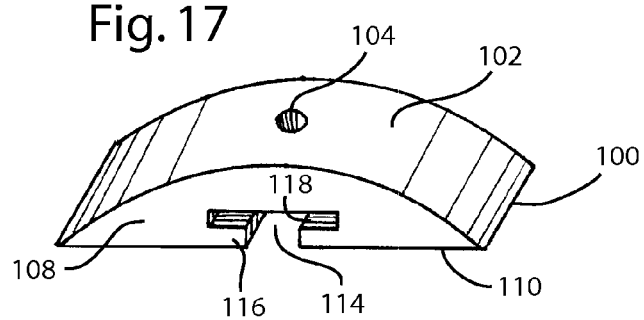
FIG. 17 shows a perspective view of an embodiment of an arcuate body of an intervertebral disc replacement device.

FIGS. 15-17 show an embodiment of the convex body 22 of the intervertebral device 10. As shown, the convex body 22 includes an arcuate body 100 comprising a first surface 102 having at least one convex body coupler 104 positioned thereon. A first and second support wall 106, 108, respectively, are in communication with the first surface 102. A base 110 is in communication with the first and second support walls 106, 108. In the illustrated embodiment, the base 110 is in communication with the first surface 102. In an alternate embodiment, the base 110 may not contact the first surface 102. At least one fastener recess 112 is positioned on the first support wall 106. Optionally, a fastener recess may be positioned on the second support wall 108 or the base 110. The fastener recess 112 is configured to receive a coupling member 23 (see FIG. 2) therein, thereby detachably coupling the convex body 22 to the second anchor plate 20.

The convex body member 120 includes an engagement surface 122 capable of movably engaging the concave recess 60 of the first implantable member 12 (see FIG. 6). A coupling surface 124 may be positioned adjacent to the engagement surface 122 and may include at least one coupling fastener 126 thereon. The coupling fastener 126 is configured to engage and be retained within the convex body coupler 104 of the arcuate body 100. In the illustrated embodiment, the coupling fastener 126 detachably couples the convex body member 120 to the first surface 102 of the arcuate body 100. Optionally, the coupling fastener 126 may non-detachably couple the convex body member 120 to the first surface 102 of the arcuate body 100. A variety of coupling fasteners 126 known in the art may be used to couple the convex body member 120 to the arcuate body 100, including, for example, pins, slip-fit retainers, friction retainers, snap-locks, and twist locks. In another embodiment, the convex body member 120 and the arcuate body 100 may be integral or joined to the arcuate body 100 using methods known in the art, including, for example, adhesively coupled, spin welded, sonic welded, over-casted, and insert molded, and may include integral features such as undercut holes and grooves thereon.

Referring to FIGS. 16 and 17, at least the second support wall 108 of the arcuate body 100 includes an attachment mechanism or attachment recess 114 configured to engage the convex body receiver 82 positioned on the interior surface 84 of the second anchor plate 20 (see FIG. 13), thereby detachably coupling the convex body 22 to the second anchor plate 20. A coupling member 23 may be positioned within the fastener recess 112 of the convex body 22 and fastener receiver 94 of the second anchor plate 20 to secure the convex body 22 to the second anchor plate 20. In the illustrated embodiment, an attachment aperture 116 and retaining recess 118 cooperatively couple the convex body 22 to the second anchor plate 20. In the alternative, a variety of coupling mechanism may be used to couple the convex body 22 to the second anchor plate 20, including, for example, magnetic coupling devices, twist locks, snap fit devices, friction fit devices, lock tabs, and other coupling mechanisms known in the art. In the illustrated embodiment, the convex body 22 is configured to slidably engage and couple to the second anchor plate 20 along the lateral axis. In an alternate embodiment, the convex body 22 may be configured to slidably engage and couple the second anchor plate 20 along the longitudinal axis $L_o$.

Figure 18:
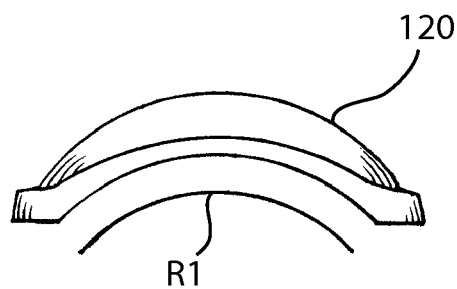
FIG. 18 shows an embodiment of a convex body member of an intervertebral disc replacement device.
Figure 19:
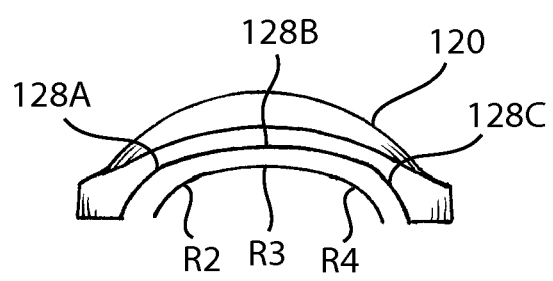
FIG. 19 shows another embodiment of a convex body member of an intervertebral disc replacement device.

The curvature and shape of surface 102 of the arcuate body 100 may be determined by the required thickness and surface curvature of the convex body member 120. The radius of curvature of the convex body 22 of the second implantable member 20 may be constant or may vary along a longitudinal convex arc A3, a lateral convex arc A4, or both. FIG. 18 shows an embodiment of the convex body member 120 having a substantially constant radius of curvature R1. In the alternative, FIG. 19 shows an embodiment of the convex body member 120 having a variable radius of curvature. As shown, the proximal region 128A has a radius of curvature R2, the medial region has a radius of R3, and the distal region has a radius of curvature R4, wherein radii R2 and R4 are greater than radius R3. Similarly, the concave recess 60 (see FIG. 4) may include a substantially constant radius of curvature or, in the alternative, may be variable as described above.

Figure 20:
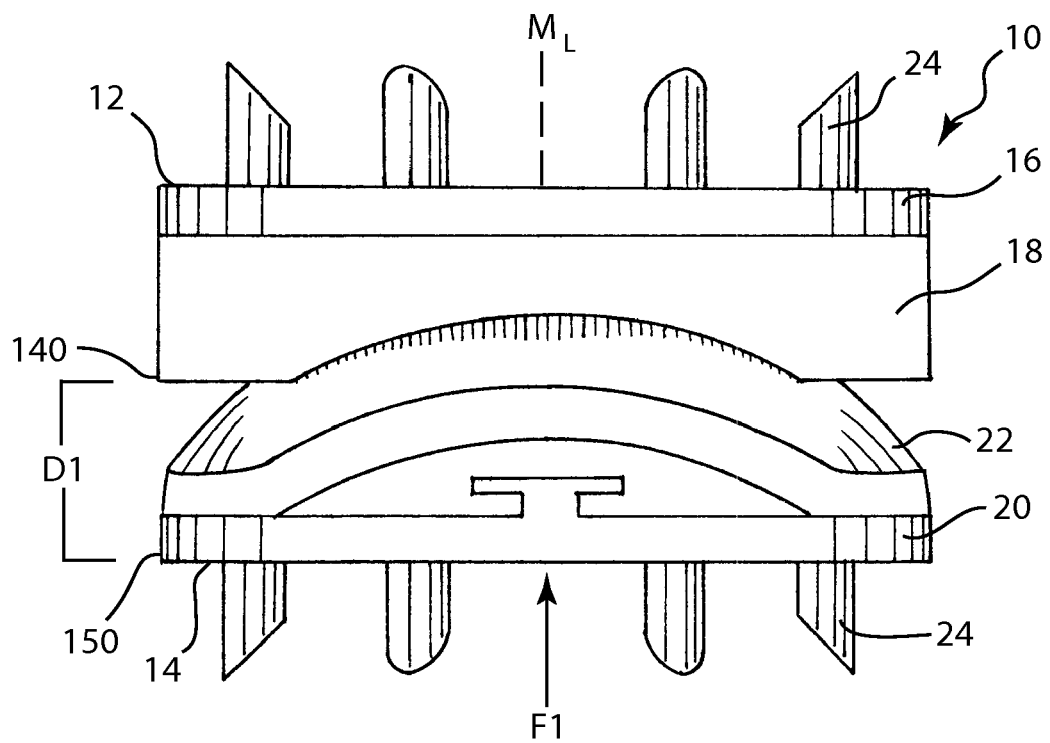
FIG. 20 shows a longitudinal side view of an embodiment of an intervertebral disc replacement device having a force applied thereto along a mid-line.
Figure 21:
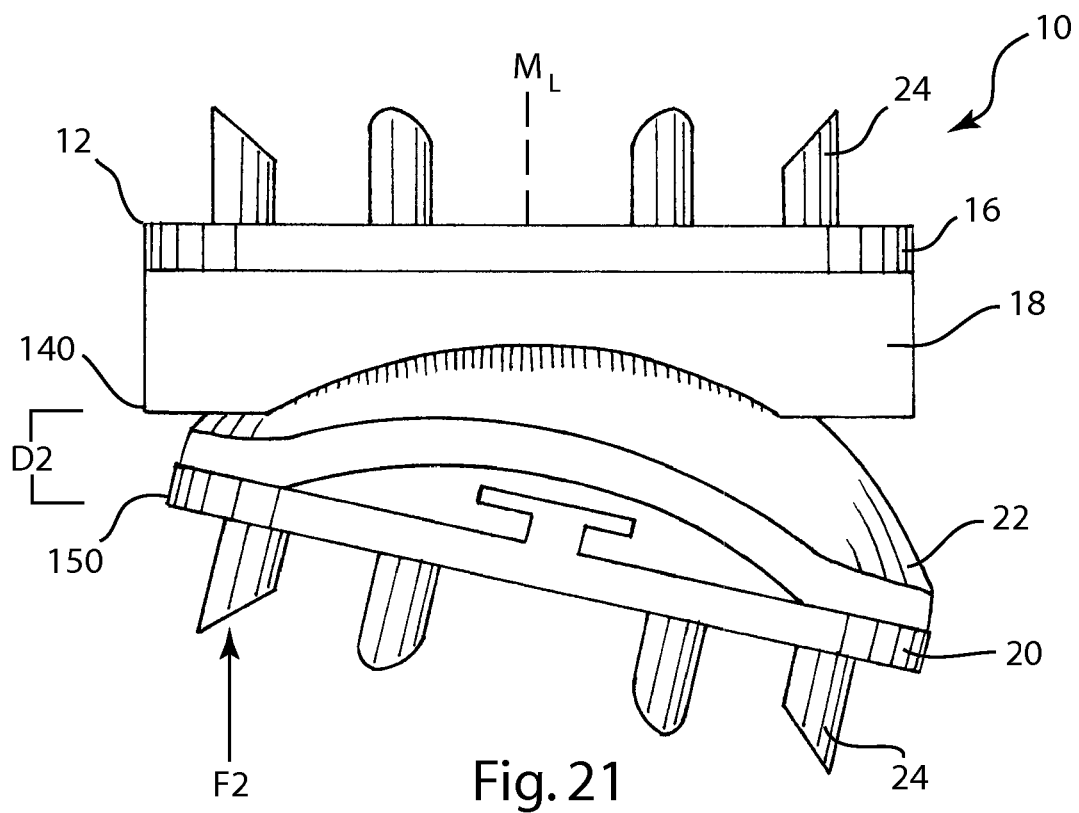
FIG. 21 shows a longitudinal side view of an embodiment of an intervertebral disc replacement device shown in FIG. 20 having a force applied thereto displaced from a mid-line.

FIGS. 20 and 21 illustrate the intervertebral device 10 during use. FIG. 20 shows an embodiment of the second implantable member 14 engaging the first implantable member 12. As shown, the convex body 22 attached to the second anchor plate 20 is positioned within and engaging the concave body 18 coupled to the first anchor plate 16. One or more anchoring elements 24 are positioned on the first and second anchor plates 16, 20, respectively. A force F1 is applied to the medial region 152 of the second implantable member 14 along the mid-line $M.sub.1$ of the intervertebral device 10. As a result, the proximal region of the first implantable member 12 is separated a distance D1 from the proximal region 150 of the second implantable member 14.

When the application of a force F2 is displaced from the mid-line $M.sub.1$ of the intervertebral device 10, the second implantable member 14 rotates within the first implantable member 12. As shown in FIG. 21, a force F2 is applied to the second implantable member 14 proximate to the proximal region 150. As a result, the convex body 22 coupled to the second anchor plate 20 rotates within the concave body 18 attached to the first anchor plate 16. As a result, the proximal region of the first implantable member 12 is separated a distance D2 from the proximal region 150 of the second implantable member 14, wherein distance D2 is less than distance D1. As shown, the movement of the second implantable member 14 within the first implantable member 12 may be unconstrained, thereby providing an intervertebral device 10 having a large range of motion along the longitudinal axis, the lateral axis, or both.

Figure 22:
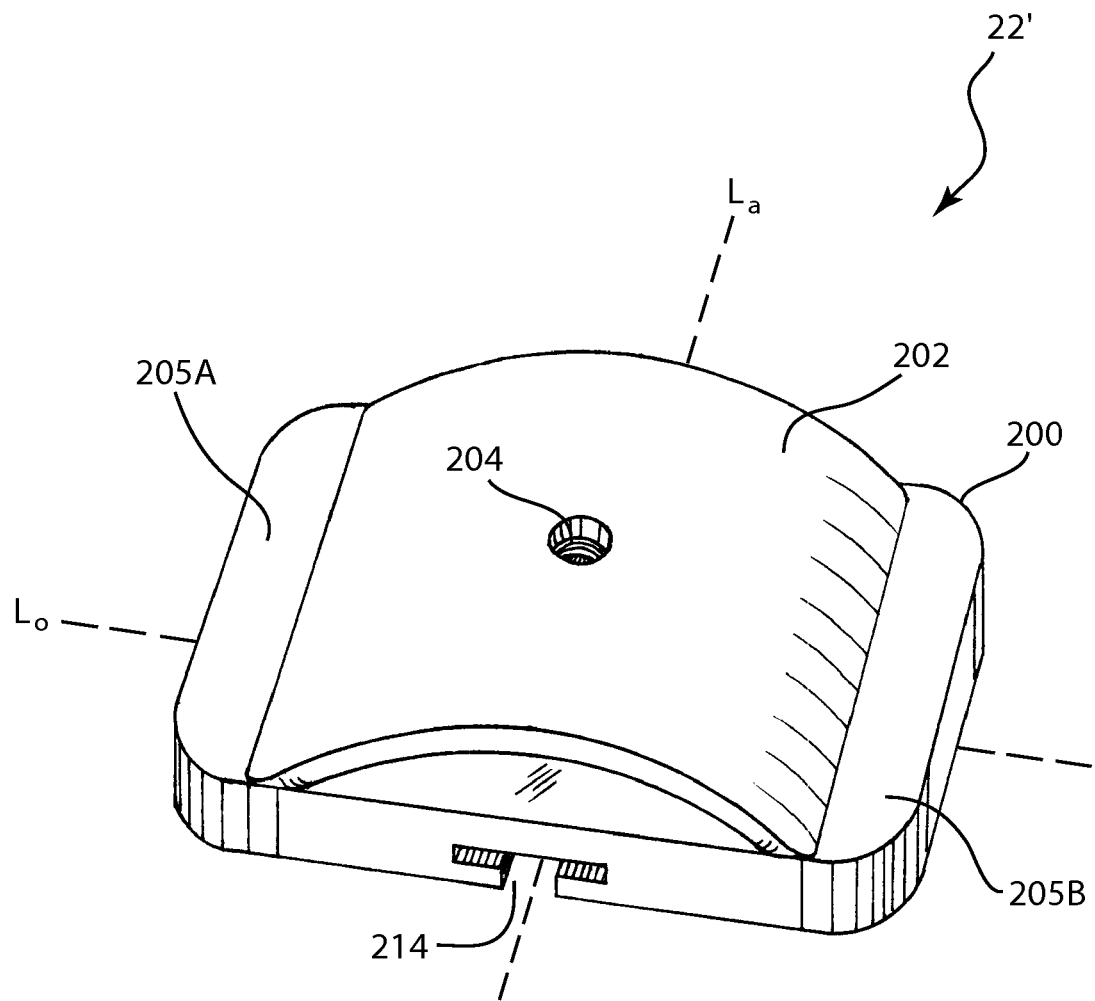
FIG. 22 shows another embodiment of a convex body of an intervertebral disc replacement device.
Figure 23:
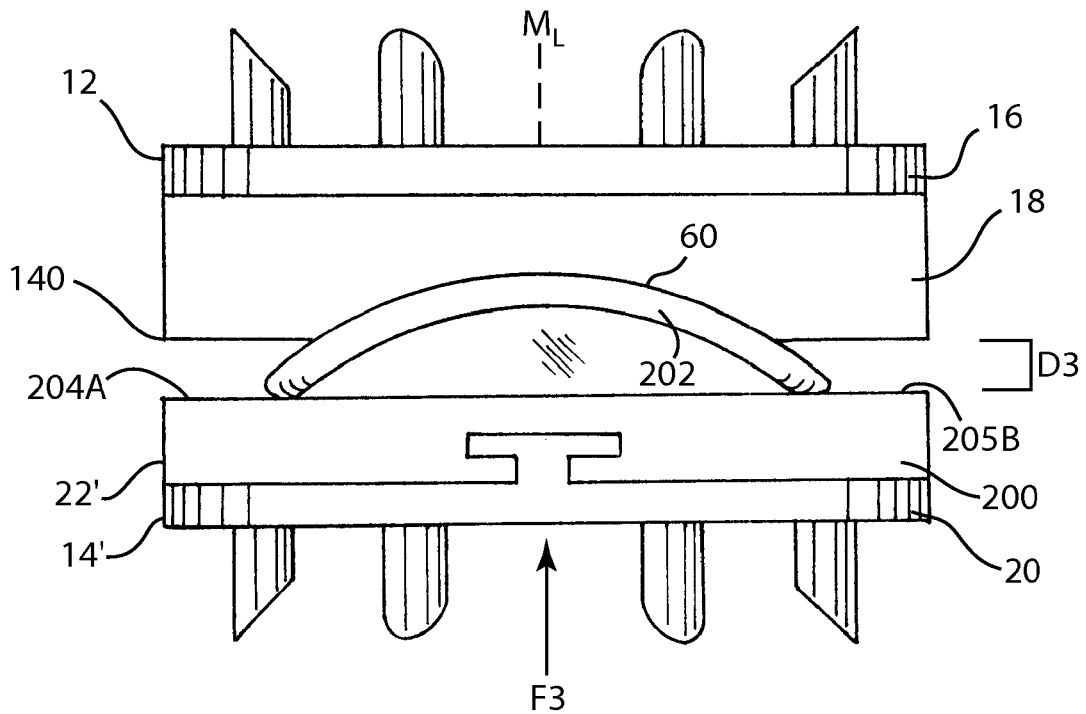
FIG. 23 shows a longitudinal side view of an embodiment of an intervertebral disc replacement device shown in FIG. 22 having a force applied thereto along a midline.
Figure 24:
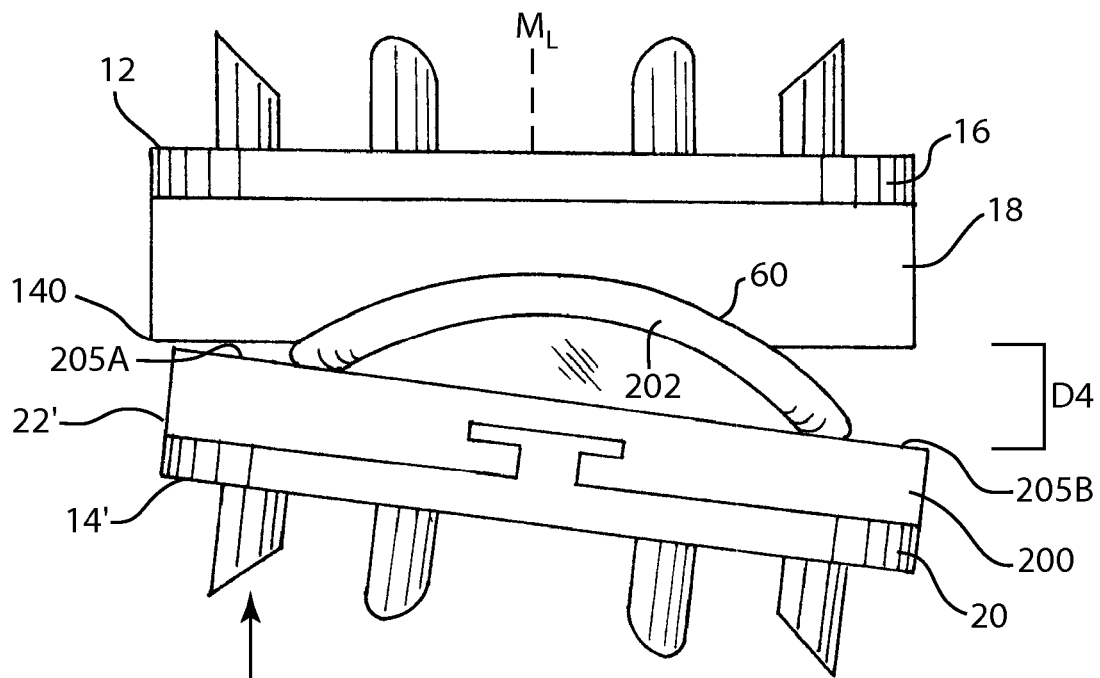
FIG. 24 shows a longitudinal side view of an embodiment of an intervertebral disc replacement device shown in FIG. 22 having a force applied thereto displaced from a mid-line.

FIGS. 22-24 show an alternate embodiment of the convex body member 22' wherein the rotational movement of the second implantable member 14' within the first implantable member 12 is constrained, limited, or restricted. As shown in FIG. 22, the constrained convex body 22' includes a body 200 having an arcuate body 202 positioned thereon. In one embodiment, the arcuate body 202 is integral to the body 200. In an alternate embodiment, the arcuate body 202 is detachably coupled to the body 200 using a variety of coupling mechanisms, including, for example, screws, bolts, pins, and adhesives. The arcuate body 202 may include a convex body coupler 204 configured to receive a coupling fastener 126 of a convex body member 120 (see FIG. 16) therein. The body 200 includes an attachment recess 214 formed therein configured to engage and retain the convex body receiver 82 of the second anchor plate 20 therein (see. FIG. 13). At least one constraining flange may be positioned on the body 200. In the illustrated embodiment, a first constraining flange 205A and a second constraining flange 205B are positioned along the longitudinal axis $L.sub.o$ of the body 200. In an alternate embodiment, one or more constraining flanges 205A, 205B may be positioned along the lateral axis $L.sub.a$ of the body 200.

As shown in FIGS. 23 and 24, the constrained convex body 22' may be coupled to the second anchor plate 20. The arcuate body 202 may be inserted into and engage the concave recess 60 of the first implantable member 12. FIG. 23 shows a force F3 applied to the first implantable member 12 and the constrained implantable member 14' along the midline $M.sub.1$. The second constraining flange 205b is positioned a distance D3 from the first implantable member 12. As shown in FIG. 24, when the application of force F4 is displaced from the midline $M.sub.1$, the first constraining flange 205A engages the concave proximal region 140, thereby limiting the maximum distance D4 the second constraining flange 205B may become displaced from the first implantable member 12.

Figure 25:
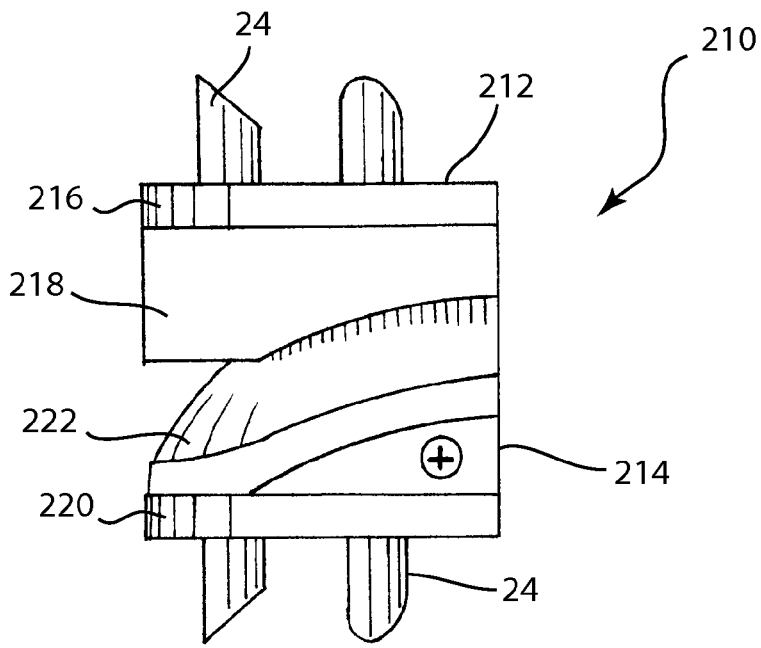
FIG. 25 shows an embodiment of a partial disc replacement device.
Figure 26:
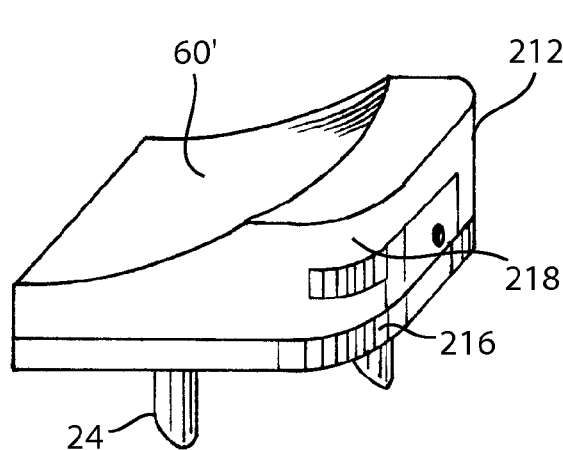
FIG. 26 shows an embodiment of a first partial disc member of a partial disc replacement device.
Figure 27:
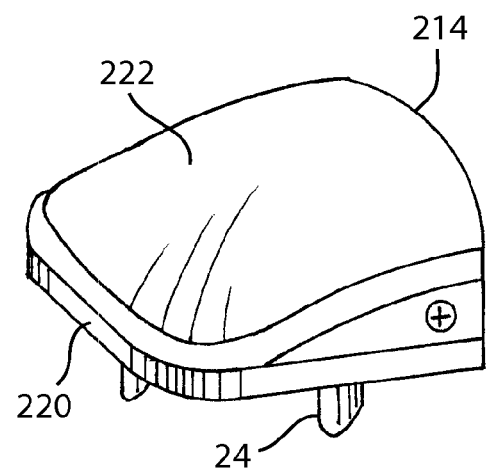
FIG. 27 shows an embodiment of a second partial disc member of a partial disc replacement device.

FIGS. 25-27 show an alternate embodiment of an intervertebral device. As shown, the partial or hemi disc device 210 may be used to replace a portion of a damaged (e.g. partially ruptured disc), diseased (e.g. scoliosis), or otherwise incompetent vertebrae. Like the intervertebral device 10 shown in FIG. 1, the partial disc device 210 comprises a first partial disc member 212 and a second partial disc member 214. Like the first implantable member 12 described above, the first partial disc member 212 includes a first anchor plate 216 detachably coupled to a hemi-concave body 218. One or more anchoring elements 24 may be used to attach the first partial disc device to the anatomical structures within a patient. For example, the anchoring elements may be capable of engaging and coupling the first partial disc device 212 to the end plates of a vertebra. Similarly, the second partial disc device 214 comprises a second anchor plate 220 having one or more anchoring elements 24 positioned thereon and detachably coupled to a hemi-convex body 222. The hemi-concave body 218 and hemi-convex body 222, respectively, may be coupled to the first and second anchor plates 216, 220, respectively, using coupling devices known in the art. For example, the coupling devices and methods described above may be used to couple the hemi-concave body 218 and hemi-convex body 222, respectively, to the first and second anchor plates 216, 220.

The intervertebral device 10 may be implanted within the spine of a patient using a variety of surgical techniques known in the art. For example, in one embodiment, an anterior lateral approach may be used to access an area of repair within a lumbar region (e.g. L2-L5) of a patient's spine will be described, although a variety of surgical techniques may be used to implant the intervertebral device within the spine of a patient. The patient may be positioned in a lateral decubitus position with the patient's spine perpendicular to the operating table. In one embodiment, the patient's shoulders and hips may be stabilized to ensure the spine remains absolutely perpendicular to the surgical table. For example, the patient's shoulders and hips may be strapped or otherwise secured to the surgical table.

Thereafter, reference alignment marks may be made on the skin of the patient and an x-ray, for example, an AP/LAT x-ray of the patient's spine may be taken to mark disc position. Once the position of the disc has been determined and marked an incision may be made directly over or proximate to the disc space. The length of the incision may vary depending upon the anatomical features of the patient. In one embodiment, and incision of about 2.5 cm to about 10 cm may be made in the skin of the patient. The incision may made from a medial position, traverse a medial plane, and terminate in a lateral position. In another embodiment, the center of the incision may extend from a mid-axillary line about 2.5 cm medially and extend 2.5 cm laterally over the disc space to be repaired (e.g. L5-S1). The incision is carried through the subcutaneous tissue to the underlying fascia. In addition, the external oblique muscle may be bluntly split along the fibers. A similar blunt dissection may be formed in the transversus and internal oblique muscles.

Thereafter, the peritoneum is identified and a blunt dissection may be made therein. The blunt dissection of the peritoneum may be carried posteriorly to the vertebral bodies of the patient's spine. A self-retaining retraction device may be inserted into the area to retain the surrounding muscles and to provide access to the repair site. The psoas over the vertebral body to be repaired is identified and a blunt dissection or muscle splitting incision is made therein. The dissection or incision may be carried anteriorly and posteriorly to isolate the disc space and the end plate of the vertebrae, without injuring lumbosacral plexus or the nerve root from the surrounding structures. Retractors may be inserted into the area of interest to isolate the disc space. For example, Stiemman pins or Horner retractors may be further stabilize the area of interest.

The dissection of the tissue is continued and the peritoneum is retracted medially and cephalad, and caudal vertebral bodies. Optionally, the peritoneum may be retracted caudal to the vertebral bodies to be repaired. With the peritoneum retracted, the segmented vessels may be, but need not be, ligated and reflected medially and laterally, thereby permitting the disc space to be identified. The dissection may be continued anteriorly and posteriorly to further isolate the disc space. Retractors, such as Horner retractors or Stiemman pins with flanges, may be placed proximate to the disc space, thereby providing anterior and posterior access to the vertebral disc.

FIGS. 28-35 show one method of inserting the intervertebral device 10 into the spine of a patient. As shown in FIG. 28, an injured disc 250 is positioned between two adjacent vertebras. Vertebras L4 and L5 are shown in FIGS. 28-30, however, those skilled in the art will appreciate that the intervertebral device 10 may be inserted at a variety of locations within the spine of a patient. The outer annulus fibrosis is elevated off the end plates and the nucleus pulposus is removed with annulus from the injured disc 250, thereby permitting the injured disc to be removed. As shown in FIGS. 29 and 30, the adjacent vertebras L4, L5 are spread a distance D6 and the injured disc 250 is removed form the disc space. Debris, such as osteophytes or residual disc material may be removed from the disc space.

With the disc space cleared of debris, the components of the intervertebral device 10 may be inserted in the patient's spine. As shown in FIGS. 31 and 32, the second implantable member 14 may be positioned in the disc space and inserted into the vertebra L4 such that the anchoring elements 24 engage and are secured within the endplates of the vertebra. With the second implantable member 14 secured to the vertebra L4, the first implantable member 12 may be inserted into the adjacent vertebra L5. As shown in FIGS. 33-35, the first implantable member 12 may be positioned in the disc space and the anchoring elements 24 made to engage and be secured to the endplates of the vertebra L5. During the implantation process, the position of the first and second implantable members 12,14 relative to the vertebra and surrounding anatomical structures may be monitored using, for example, x-rays, IVUS, and echo-locative devices. In the illustrated embodiment, the second implantable member 14 is inserted prior to insertion of the first implantable member 12, and is inserted cephalad to the first implantable member 12. Those skilled in the art will appreciate that order of implantation and position of implantation devices 12, 14 relative to each other may be varied and should not be considered as limited to the order and position described above.

FIGS. 36-40 show the replacement of a component of the intervertebral device 10 when implanted. FIG. 36 shows the intervertebral device 10 having a first implantable member 12 and a second implantable member 14 implanted into vertebras L4 and L5. To replace a component of the intervertebral device 10, the adjacent vertebras L4, L5 are separated to permit access to the implanted intervertebral device 10. Thereafter, the coupling device 23 securing the concave body 18 or the convex body 22 to the first or second anchor plate 16, 20, respectively, is removed. As shown in FIGS. 37 and 38, with the coupling device 23 removed the convex body 22 may be detached from the second anchor plate 20, thereby leaving the second anchor plate 20 coupled to the vertebra L4. Thereafter, as shown in FIGS. 39 and 40, a replacement convex body 22 may be positioned within the disc space. The attachment recess 114 on the replacement convex body 22 may engage and be retained by the convex body receiver 82 positioned on the second anchor plate 20, thereby coupling the replacement convex body 22 to the second anchor plate 20. Once coupled, a coupling device 23 may be inserted into the fastener recess 12 on the replacement convex body 22 and secured in the fastener receiver 94 of the second anchor plate 20. The concave body 18 of the first implantable member 12 may be separated from the first anchor plate 16 and replaced in a similar manner as described above.

In an alternate embodiment, the concave body 18 and the convex body 22 may be removed from the first and second anchor plates 16, 20, respectively, and replaced with a disc fusion device, thereby fusing the vertebras L4 and L5. As shown in FIG. 41, the first and second implantable members 12, 14 and implanted within the vertebras L4, L5 and separated by a distance D7. Thereafter, vertebras L4, L5 may be separated a distance D8 to provide access to the disc space. Once separated, the coupling members 23 may be removed from the first and second implantable members 12, 14, thereby permitting the concave body 18 to be removed from the first anchor plate 16, and the convex body 22 to be removed from the second anchor plate 20. As shown in FIG. 42, the first and second anchor plates 16, 20 remain attached to the vertebras L4, L5. Thereafter, a fusion device 260 may be inserted into the disc space and coupled to the first and second anchor plates 16, 20 with one or more coupling members 23, thereby fusing vertebras L4 and L5 together. Exemplary fusion or implantation devices capable of coupling to the first and second anchor plates 16, 20 are disclosed in U.S. Pat. No. 6,113,638, issued to Lytton A. Williams, the entire disclosure of which is hereby incorporated by reference in its entirety. According to one example, the fusion device 260 may have a configuration similar to that of the spacer 116 of FIG. 5D of U.S. Pat. No. 6,113,638, with one or more cavities like the hollow bores 119 that communicate with one or both of the adjacent vertebral bodies.

Once the intervertebral device 10 had been implanted, the surgeon may remove the retractors to permit the peritoneum to return to a natural position. Prior to closing the surgical site, the surgeon may administer a therapeutic agent to the vertebras, the peritoneum, or the surrounding tissue. Thereafter, the subcutaneous tissue is closed and sutured.

In closing, it is understood that the embodiments of the invention disclosed herein are illustrative of the principals of the invention. Other modifications may be employed which are within the scope of the present invention. Accordingly, the present invention is not limited to that precisely as shown and described in the present disclosure.

The invention claimed is:

1. A method of revising an intervertebral implant on a spine comprising first and second vertebral bodies adjacent to an intervertebral space, the intervertebral implant comprising a first anchor plate secured to the first vertebral body, a second anchor plate secured to the second vertebral body, and a first intermediate component positioned at least partially between the first and second anchor plates, the first intermediate component comprising a concave body attached to the first anchor plate, the concave body having a concave recess shaped to articulate with a convex surface to permit relative motion between the first and second anchor plates, the method comprising:
    detaching the concave body from the first anchor plate without removing the first anchor plate from the first vertebral body; and
    removing the concave body from the intervertebral space.

2. The method of claim 1, wherein the intervertebral implant further comprises an anchoring element positioned on the first anchor plate to enhance securement of the first anchor plate to the first vertebral body by penetrating the first vertebral body, wherein detaching the concave body from the first anchor plate comprises avoiding withdrawing the first anchoring element from penetration of the first vertebral body.

3. The method of claim 2, wherein the first anchoring element is attached to the first anchor plate independently of any threaded connection.

4. The method of claim 3, wherein the first anchoring element is formed as a single piece with the first anchor plate.

5. The method of claim 2, wherein the first anchoring element comprises a sharp point.

6. The method of claim 1, wherein the intervertebral implant further comprises a coupling member, wherein detaching the concave body from the first anchor plate comprises actuating the coupling member to permit removal of the concave body from the first anchor plate without requiring access to a bone-engaging surface of the first anchor plate.

7. The method of claim 6, wherein the coupling member comprises a set screw, wherein actuating the coupling member comprises disengaging threads of the set screw from threads of the first anchor plate.

\* \* \* \* \*